(12) United States Patent
Souza et al.

(10) Patent No.: US 8,630,473 B2
(45) Date of Patent: Jan. 14, 2014

(54) NOISE SUPPRESSION IN CONE BEAM CT PROJECTION DATA

(71) Applicants: Andre Souza, Webster, NY (US); Peter D. Burns, Fairport, NY (US)

(72) Inventors: Andre Souza, Webster, NY (US); Peter D. Burns, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 13/693,180

(22) Filed: Dec. 4, 2012

(65) Prior Publication Data

US 2013/0094746 A1    Apr. 18, 2013

Related U.S. Application Data

(62) Division of application No. 12/644,287, filed on Dec. 22, 2009, now Pat. No. 8,346,007.

(51) Int. Cl.
*G06K 9/00* (2006.01)
*G06K 9/40* (2006.01)

(52) U.S. Cl.
USPC ............ 382/131; 382/132; 382/154; 382/275

(58) Field of Classification Search
USPC .................................. 382/131, 132, 154, 275
See application file for complete search history.

(56) References Cited

U.S. PATENT DOCUMENTS

| 5,170,439 | A | 12/1992 | Zeng et al. |
| 5,999,587 | A | 12/1999 | Ning et al. |
| 6,501,848 | B1 | 12/2002 | Carroll et al. |
| 8,229,199 | B2 | 7/2012 | Chen et al. |
| 8,306,302 | B2 | 11/2012 | Souza et al. |
| 2004/0012611 | A1 | 1/2004 | Taneja et al. |
| 2009/0052796 | A1 | 2/2009 | Furukawa et al. |

OTHER PUBLICATIONS

Lei Zhu, et al., "Noise suppression in scatter correction for cone-beam CT," Med. Phys., vol. 36, No. 3, Mar. 2009, pp. 741-752.
Jessie Q. Xia, et al., "Dedicated breast computed tomography: Volume image denoising via a partial-diffusion equation based technique," Med. Phys., vol. 35, No. 5, May 2008, pp. 1950-1958.
Perona and Malik, "Scale-Space And Edge Detention Using Anisotropic Diffusion", IEEE Trans. Pattern Analysis. Machine Intelligence, 1990, vol. 12, pp. 629-639.

*Primary Examiner* — Anand Bhatnagar
*Assistant Examiner* — Soo Park

(57) ABSTRACT

A method for suppressing noise in a diagnostic 3-D image, executed at least in part on a logic processor, captures, at each of a number of projection angles, 2-D image projection data, wherein each 2-D image projection has a central pixel and arranges the 2-D image projection data to form a 3-D data set. Each of the 2-D image projections is processed by performing a diffusion filtering process that obtains a homogeneity value for the 3-D data set, generates a diffusion conductance function according to an intensity gradient between adjacent digital image elements, and applies the diffusion filtering process to digital image elements according to the obtained homogeneity value, the generated diffusion conductance function, and a weighting value that relates to the distance of each pixel in the projection from the central pixel. The diagnostic 3-D image is reconstructed from the processed 2-D image projections.

8 Claims, 13 Drawing Sheets

NOISE SUPPRESSION IN CONE BEAM CT PROJECTION DATA

CROSS REFERENCE TO RELATED APPLICATIONS

This application is a Divisional of U.S. Ser. No. 12/644,287 filed Dec. 22, 2009 to Souza et al, entitled NOISE SUPPRESSION IN CONE BEAM CT PROJECTION DATA, incorporated herein in its entirety.

FIELD OF THE INVENTION

The invention relates generally to the field of diagnostic imaging and more particularly relates to a method for noise suppression for images obtained from cone-beam projection data.

BACKGROUND OF THE INVENTION

Noise is often present in acquired diagnostic images, such as those obtained from computed tomography (CT) scanning and other x-ray systems, and can be a significant factor in determining how well real intensity interfaces and fine details are preserved in the image. In addition to influencing diagnostic functions, noise also affects many automated image processing and analysis tasks that are crucial in a number of diagnostic applications.

Methods for improving signal-to-noise ratio (SNR) and contrast-to-noise ratio (CNR) can be broadly divided into two categories: those based on image acquisition techniques and those based on post-acquisition image processing. Improving image acquisition techniques beyond a certain point can introduce other problems and generally requires increasing the overall acquisition time. This risks delivering a higher X-ray dose to the patient and loss of spatial resolution and may require the expense of scanner equipment upgrade.

Post-acquisition filtering, an off-line image processing approach, is often as effective as improving image acquisition without affecting spatial resolution. If properly designed, post-acquisition filtering requires less time and is usually less expensive than attempts to improve image acquisition. Filtering techniques can be classified into two groupings: (i) enhancement, wherein wanted (structure) information is enhanced, ideally without affecting unwanted (noise) information, and (ii) suppression, wherein unwanted information (noise) is suppressed, ideally without affecting wanted information. Suppressive filtering operations may be further divided into two classes: a) space-invariant filtering, and b) space-variant filtering.

Space-invariant filtering techniques, wherein spatially independent fixed smoothing operations are carried out over the entire image, can be effective in reducing noise, but often blur important structures or features within the image at the same time. This can be especially troublesome because details of particular interest often lie along an edge or a boundary of a structure within the image, which can be blurred by conventional smoothing operations.

Space-variant filtering techniques, meanwhile, are less likely to cause blurring of the image. Various methods using space-variant filtering, wherein the smoothing operation is modified by local image features, have been proposed. Diffusive filtering methods based on Perona and Malik's work (1990) [Perona and Malik, "Scale-space and edge detection using anisotropic diffusion", *IEEE Trans. Pattern Analysis. Machine Intelligence,* 1990 vol. 12, pp. 629-639] have been adapted to a number of image filtering applications. Using these methods, image intensity at a pixel is diffused to neighboring pixels in an iterative manner, with the diffusion conductance controlled by a constant intensity gradient for the full image. The approach described by Perona and Malik uses techniques that preserve well-defined edges, but apply conventional diffusion to other areas of the 2-D image. While such an approach exhibits some success with 2-D images, however, there are drawbacks. One shortcoming of this type of solution relates to the lack of image-dependent guidance for selecting a suitable gradient magnitude. More particularly, since morphological or structural information is not used to locally control the extent of diffusion in different regions, fine structures often disappear and boundaries that are initially somewhat fuzzy may be further blurred upon filtering when this technique is used.

Three-dimensional imaging introduces further complexity to the problem of noise suppression. Conventional computed tomography CT scanners direct a fan-shaped X-ray beam through the patient or other subject and toward a one-dimensional detector, reconstructing a succession of single slices to obtain a volume or 3-D image. Cone-beam computed tomography or CBCT scanning makes it possible to improve image capture and processing speeds by directing a cone-beam source toward the subject and obtaining the image on a flat-panel X-ray detector. In cone-beam computed tomography scanning, a 3-D image is reconstructed from numerous individual scan projections, each taken at a different angle, whose image data is aligned and processed in order to generate and present data as a collection of volume pixels or voxels.

CBCT scanning is of interest for its advantages in biomedical, dental, and industrial applications. As flat-panel digital x-ray detectors improve in usability and performance, with reduction in image acquisition speed, CBCT shows promise in providing 3-D imaging capabilities at higher image resolution using lower overall radiation dose and with simplified scanner design. However, image noise remains a problem. Using conventional diffusion techniques to reduce image noise can often blur significant features within the 3-D image, making it disadvantageous to perform more than rudimentary image clean-up for reducing noise content.

The processing of CBCT data for obtaining images requires some type of reconstruction algorithm. Various types of image reconstruction have been proposed, generally classified as either (i) exact, (ii) approximate, or (iii) iterative. Exact cone-beam reconstruction algorithms, based on theoretical work of a number of researchers, require that the following sufficient condition be satisfied: "on every plane that intersects the imaged object there exists at least one cone-beam source", also called the sufficient condition, to be satisfied. The widely used Grangeat algorithm, familiar to those skilled in CBCT image processing, is limited to circular scanning trajectory and spherical objects. Only recently, with generalization of the Grangeat formula, exact reconstruction is possible in spiral/helical trajectory with longitudinally truncated data.

Despite advances in exact methods (i, above), approximate methods (ii) continue to be more widely used. Chief among these CBCT reconstruction approaches and familiar to those skilled in the CT imaging arts are the Feldkamp (FDK) based algorithms.

Advantages of the FDK method include:

1) FDK based algorithms may produce better spatial and contrast resolution, since they need less regularization than do the exact reconstructions;

2) FDK processing produces improved temporal resolution. Reconstruction can be performed using either full-scan or half-scan data. The shorter scanning time improves the temporal resolution, which is critical for applications such as cardiac imaging, lung imaging, CT-guided medical intervention, and orthopaedics;

3) FDK algorithms are computationally efficient. Implementation of the FDK algorithm is relatively simple, straightforward, and processing can be executed in parallel.

The increasing capabilities of high-performance computers and advanced parallel programming techniques contribute to making iterative CBCT reconstruction algorithms (iii) more attractive. As one advantage, iterative approaches appear to have improved capabilities in handling noisy and truncated data. For instance, iterative deblurring via expectation minimization, combined with algebraic reconstruction technique (ART), has been shown to be effective in suppressing noise and metal artifacts.

Image variation is inherent to the physics of image capture and is at least somewhat a result of practical design tolerances. The discrete nature of the x-ray exposure and its conversion to a detected signal invariably results in quantum noise fluctuations. This type of image noise is usually described as a stochastic noise source, whose amplitude varies as a function of exposure signal level within a projected digital image. The resulting relative noise levels, and signal-to-noise ratio (SNR), are inversely proportional to exposure. A second source of image noise is the flat-panel detector and signal readout circuits. In many cases, image noise that is ascribed to non-ideal image capture is modeled as the addition of a random component whose amplitude is independent of the signal level. In practice, however, several external factors, such electro-magnetic interference, can influence both the magnitude and the spatial correlations of image noise due to the detector.

Noise is an inherent aspect of cone beam projection data, especially for low-dose scans. Image filtering, an image processing approach for improving SNR and contrast-to-noise ratio (CNR), is often as effective in compensating for noise as is optimizing the scanner design (hardware) without affecting the image contrast and the image spatio-temporal resolution. If properly designed, filtering requires less time and can be less expensive than improving the hardware.

Filtering methods for 2-D projection data (or sinograms) have been reported in the literature. However, as compared against 2-D considerations, the 3-D noise problem is significantly more complex and does not readily lend itself to 2-D solutions. Among problems not addressed by 2-D solutions is tangential blurring, for example, an artifact familiar to those skilled in 3-D image reconstruction and attributed to angular filtering approaches.

Thus, it is seen that there is a need for improved noise suppression filtering methods that reduce image noise in images obtained from CBCT systems, without compromising sharpness and detail for significant structures or features in the image.

SUMMARY OF THE INVENTION

It is an object of the present invention to advance the art of noise suppression in image reconstruction from CBCT image data and other types of 3-D imaging technologies that use image reconstruction.

It is a feature of the present invention that the amount of filtering is reduced proportionately to the distance between measured voxel data.

It is an advantage of the present invention that it reduces tangential blur in image reconstruction.

From one aspect, the present invention provides a method for suppressing noise in a diagnostic 3-D image, the method executed at least in part on a logic processor and comprising: capturing at each of a plurality of projection angles, 2-D image projection data, wherein each 2-D image projection has a central pixel; arranging the captured 2-D image projection data in an electronic memory to form a 3-D data set; processing the image projection data for each of the 2-D image projections of the 3-D data set by performing a diffusion filtering process that comprises: obtaining a homogeneity value for the 3-D data set; generating a diffusion conductance function according to an intensity gradient between adjacent digital image elements from the projection data; applying the diffusion filtering process to a plurality of digital image elements according to the obtained homogeneity value, the generated diffusion conductance function, and a weighting value that relates to the distance of each pixel in the projection from the central pixel; and reconstructing the diagnostic 3-D image from the processed 2-D image projection data.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. Elements of the drawings are not necessarily to scale relative to each other.

DETAILED DESCRIPTION OF THE INVENTION

Figure 1:
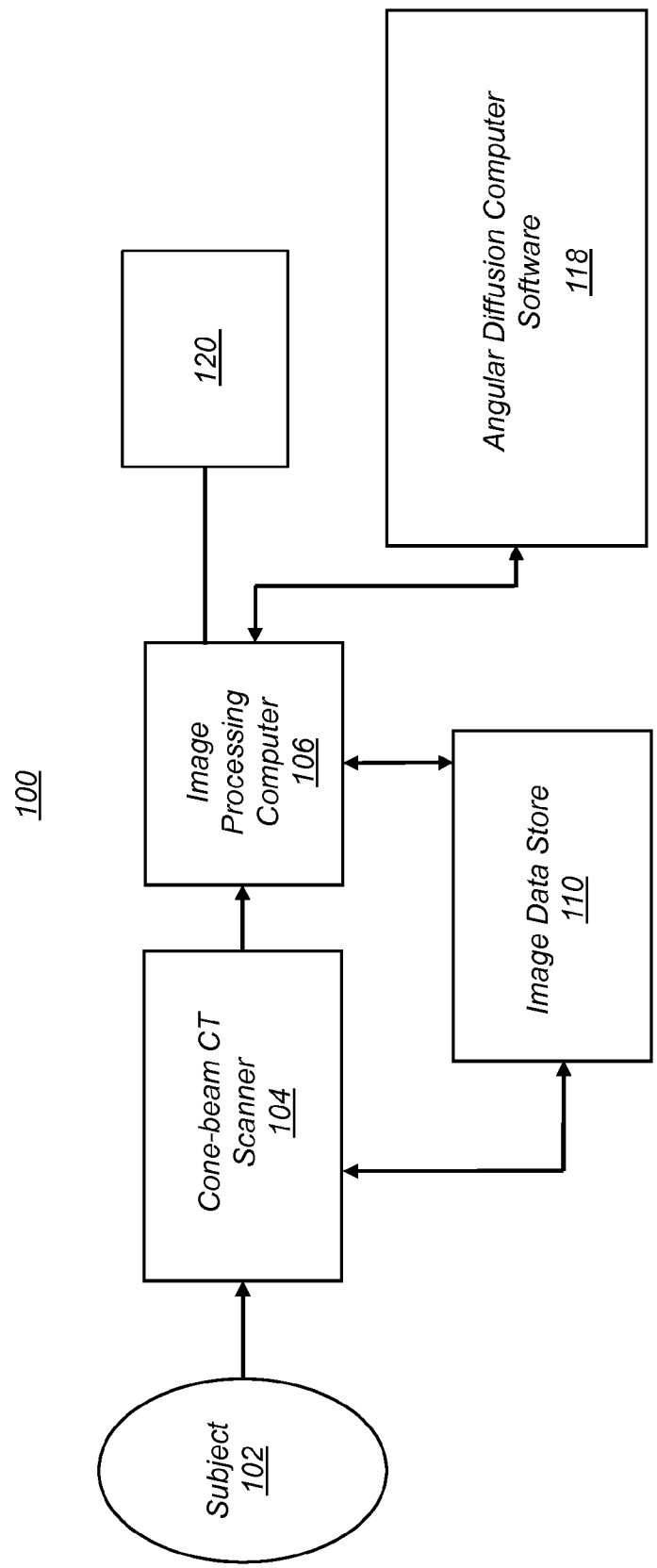
FIG. 1 is a schematic diagram showing components of an image acquisition and processing system for executing the method of the present invention in one embodiment.

The following is a detailed description of the preferred embodiments of the invention, reference being made to the figures in which the same reference numerals identify the same elements of structure in each of the figures.

The term "image element" or "digital image element" refers to a pixel (from "picture element" and commonly used for an image with two dimensions) or to a voxel (from "volume picture element" for an image of three or more dimensions). In CBCT imaging, the two types of digital image elements are closely related: 3-D voxels are formed using data obtained from pixels that were obtained in one or more 2-D projections. The terms "in-plane" and "out-of-plane" relate to the arrangement of image element data as obtained from the planar 2-D digital detector and used to form 3-D voxels.

The term "region" is used in the present application to describe an area of a 2-D image or, correspondingly, a volume of a 3-D or 4-D or higher image that contains a grouping of contiguous image elements (that is, pixels in the 2-D domain; voxels in 3-D, 4-D, or higher-dimensioned images). A region is defined by intensity characteristics of its image elements (pixels or voxels), such as where their intensity values lie within a certain range of values, for example, as well as where a grouping of pixels is bounded by discernable bounding structures or features in the image.

The term "adjacent", or "n-adjacent" where n is an integer, when used to describe an image element, pixel or voxel, indicates that two image elements are in some way contiguous. For a two-dimensional image, one pixel may be adjacent to another either at one of its 4 vertices or along any of its 4 edges. For a three-dimensional image, one voxel may be adjacent to another either at one of its 8 vertices, or along one of its 12 edges, or along one of its 6 faces (to its so-called "6-adjacent" voxels). A voxel is thus adjacent to as many as 26 neighboring voxels.

Reference is made to commonly assigned U.S. Patent Application U.S. Ser. No. 12/239,844 by Souza et al., entitled "NOISE SUPPRESSION IN DIAGNOSTIC IMAGES" filed on Sep. 29, 2008.

FIG. 1 shows components of an image acquisition and processing system 100 for executing the method of the present invention for 3-D imaging in one embodiment. Image acquisition and processing system 100 includes an imaging system, shown in the embodiment of FIG. 1 as a cone-beam CT scanner, CBCT scanner 104. The method of the present invention could alternately be used with other types of imaging systems, including 4-D, or other systems. In the FIG. 1 embodiment, CBCT scanner 104 images a subject 102, such as a patient, capturing image data to produce a volume of image data as a sequence of individual image slices. The entire set of image slices provides volume image data for the subject. The number of slices taken from one direction may vary from a few dozen to hundreds of image slices, limited by the current CT scanner resolution. The image slices are conventionally stored in an image data store 110 as a DICOM series, as reported in National Electrical Manufacturers Association (NEMA) ed.: Digital Imaging and Communications in Medicine (DICOM) Part 3, PS 3.3 (2003). These DICOM series can be referred to as pre-processed image data.

Post-processing of image data can take any of a number of forms. In one embodiment, an image processing computer 106 uses the DICOM series stored in image data store 110 to produce filtered (noise-suppressed) image slices. In the embodiment of FIG. 1, image processing computer 106 invokes angular diffusion computer software 118 that includes stored instructions arranged to provide noise-filtered image output, using an iterative sequence described in more detail subsequently. An optional display 120 then allows the processed image to be viewed.

Embodiments of the present invention provide an improved filtering method for image noise suppression in projection data for CBCT, as well as for fan beam and tomosynthesis applications. Unlike earlier filtering methods, the method of the present invention utilizes information about the geometry of image capture as it relates to the relative positions of voxels in the reconstructed image.

For an understanding of how the method of the present invention operates, it is first useful to review CBCT image acquisition and to describe coordinate assignments and geometry used in subsequent detailed description. The perspective views of FIGS. 2A and 2B and plan view (top view from along the z-axis) of FIG. 2C show concepts, terminology, and geometry that are used in the present disclosure. FIG. 2D helps to show the effect of arc length on projection data.

Figure 2A:
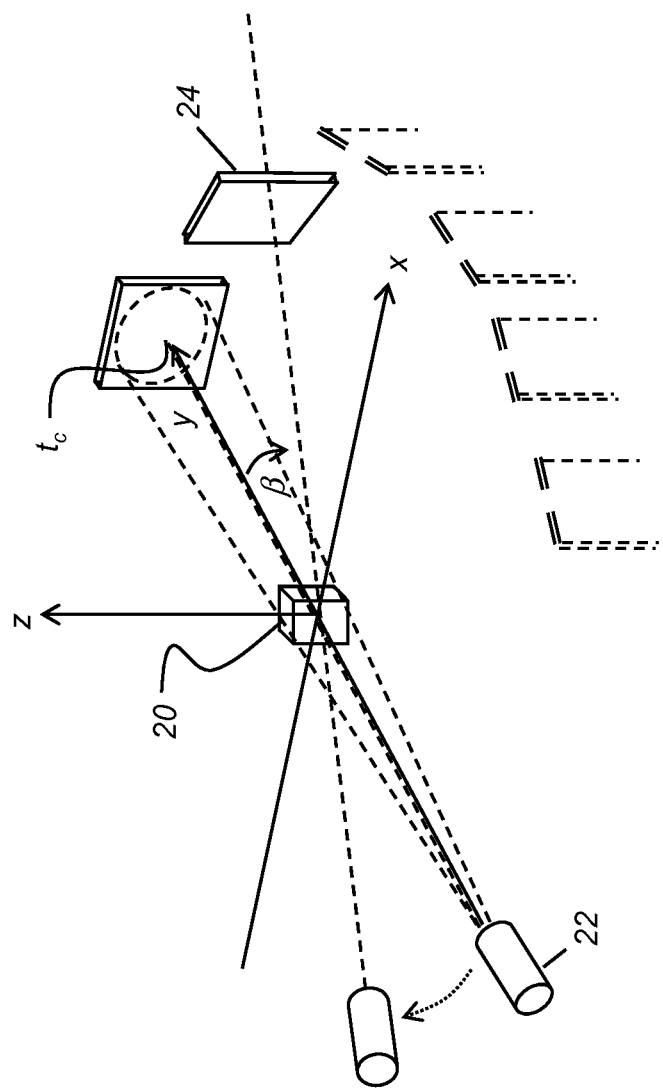
FIG. 2A is a perspective view showing how cone-beam CT projections are obtained.

Referring to FIG. 2A, the basic pattern and sequence of CBCT imaging is shown in simplified schematic form. At each of a series of positions that encircle an object 20, a cone beam source 22 directs a cone of x-rays through object 20 and onto a flat panel detector 24, such as a digital radiography (DR) receiver. This captures a 2-D projection image that is to be used in subsequent 3-D reconstruction. Source 22 and detector 24 are successively moved into each position in sequence. A number of positions are represented in phantom form in FIG. 2A; in practice, positions are typically spaced closer together than shown here, with angle β between one position and the next typically not more than a few degrees. These positions typically extend in a half-circle or circle about object 20. Detector 24 provides its image data for the component projection image to image processing computer 106 (FIG. 1) that executes the image reconstruction logic processing for generating 3-D data from the series of component 2-D cone beam projection images. In the simplest arrangement, the ray that passes directly through the center of object 20 is incident at a center point $t_c$, a central pixel on detector 24.

Figure 2B:
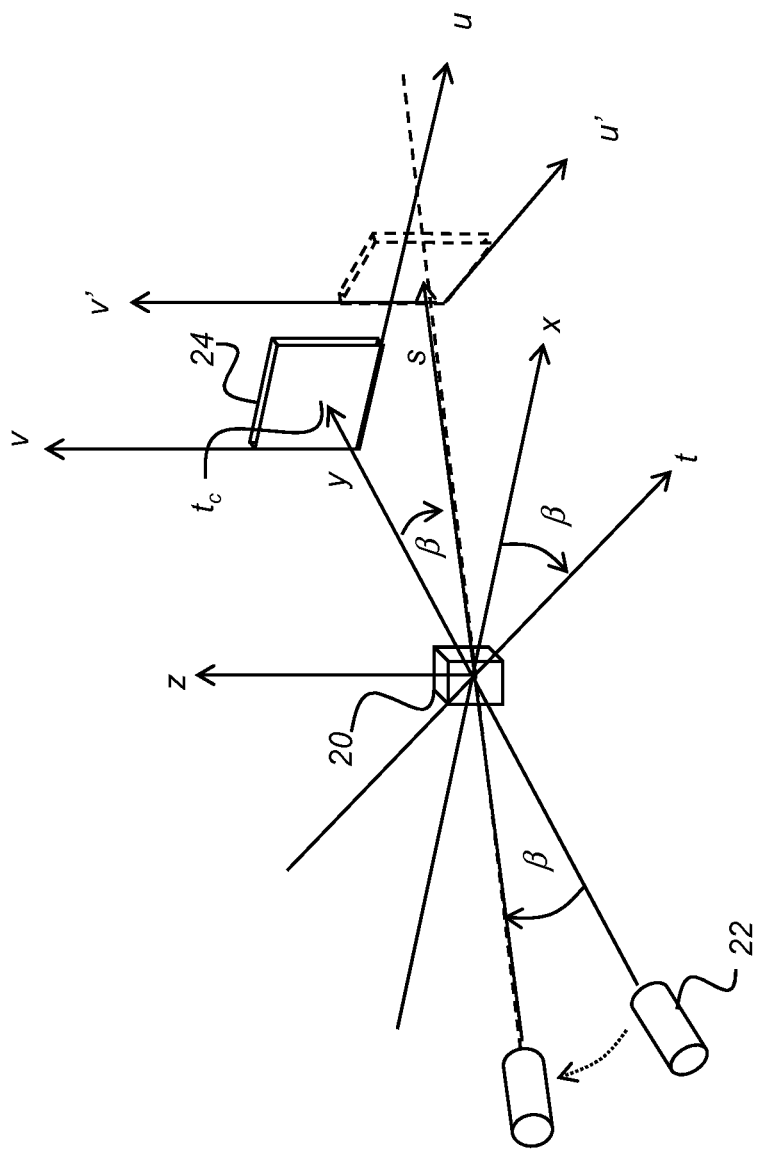
FIG. 2B is a perspective view showing coordinate designations for cone-beam CT imaging.
Figure 2C:
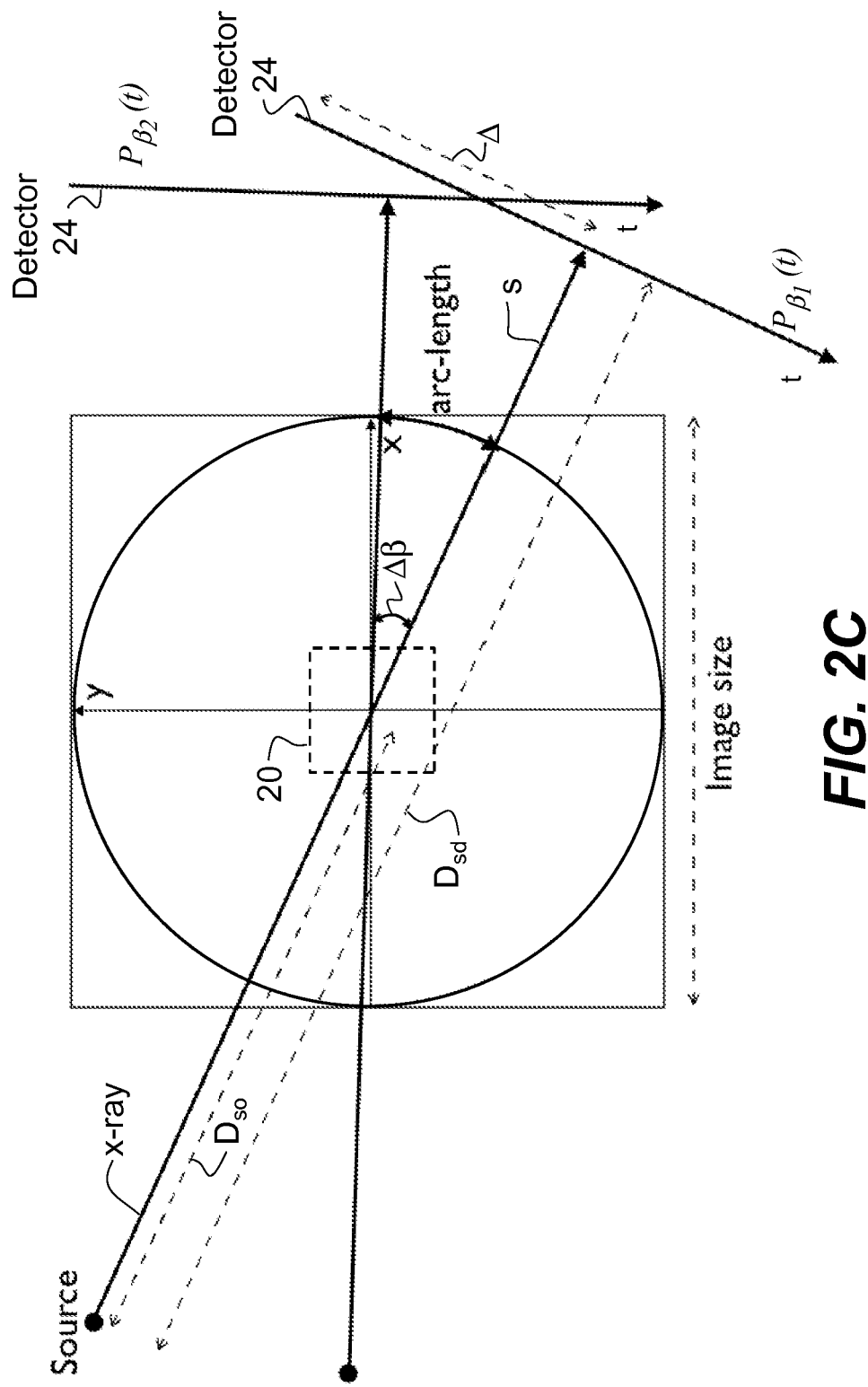
FIG. 2C is a top view, taken along the z axis, that shows a detector translated from a first to a second position.
Figure 2D:
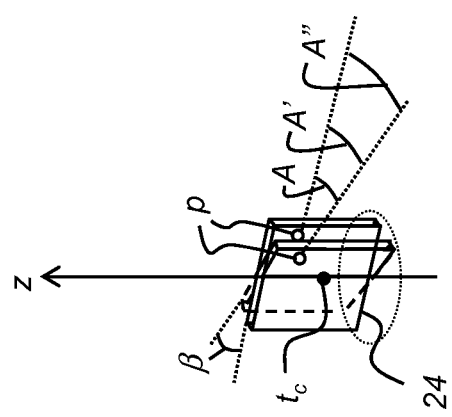
FIG. 2D is a perspective view that shows parameters related to 3-D image reconstruction.

The schematic diagram of FIG. 2B shows the coordinate system designations that are used in subsequent description. The initial reference coordinate system is the conventional Cartesian (x, y, z) coordinate system, with rotation of source 22 and detector 24 about the z axis.

As source 22 is moved from one position to the next, a rotated coordinate system (4 s, z) is used. The 2-D coordinate system of detector 24 has orthogonal axes designated v and u. FIG. 2B shows the translated detector 24 with orthogonal axes designated v' and u'.

FIG. 2C shows a top view, taken along the z axis, with detector 24 translated from a first to a second position. Represented at center is a 2-D slice from the 3-D volume. Distance $D_{so}$ is the distance from the source 22 to the center of object 20. Distance $D_{sd}$ is the distance from the source 22 to detector 24. Labels $P_\beta(t)$ designate detector positions at different angles β. The symbol Δ designates a distance of a pixel from the left edge of detector 24 to a central pixel.

A projection scene is formed as a set of planar projections $P_\beta(u, v,)$ of object 20 obtained at a number of angles β and stacked together to form a 3-D volume image. An acquired digital 3-D image projection scene is represented as a pair $C=(C, f)$, wherein:

$$C=\{c\,|\,-b_j\leq c_j\leq b_j \text{ for some } b_j\in Z_+^3\}$$

wherein $Z_+^3$ is the set of 3-tuples of positive integers called voxels, $f$ is a function whose domain, termed the scene domain, is C. The range of $f$ is a set of integers [L,H] and for any c∈$f$(c), $f$(c) is referred to as the intensity of c. whose values are the measurements of the projection data $P_\beta(u,v,)$ such that there exists a one-to-one mapping from c to (u, v, β). Domain C corresponds to a binary scene if the range of $f$ is {0,1}.

One inherent problem for any of the 3-D reconstruction techniques relates to voxel location relative to the center of the scanned subject. This problem can be more clearly shown by considering the spatial or geometric relationship of pixels in two consecutive 2-D projection images. Referring to the idealized perspective view of FIG. 2D, two detector 24 positions, for two adjacent projection images relative to the actual volume of the imaged subject, are shown as if superimposed over the subject, separated by angle β. In processing, successive projection images are arranged in an electronic memory accessible to the logic processor as a 3-D data set, with their data stacked according to the corresponding projection angle β. For this example, it is assumed that the central ray of the cone beam is incident at central pixel $t_c$ for each projection image; in actual practice, there may be an offset from the exact geometric center position for one or more projection images.

Referring to the example of FIG. 2D, central pixel $t_c$, corresponding to the central voxel of the reconstructed 3-D image, is at the center of detector 24 at each detector 24 position. Where the central x-ray of the cone is incident at pixel $t_c$, 3-D data for the central voxel that corresponds to this central pixel position can be highly accurate. However, this accuracy diminishes for portions of the imaged volume that are some distance from this central voxel. As pixels are increasingly spaced farther away from central pixel $t_c$ and closer to the edge of detector 24, there is an increased arc length between projection images for the same pixel location on the detector. Arc length increases with increasing radius. FIG. 2D shows three arc lengths A, A', and A", progressively increasing in dimension with increased distance from the central axis of rotation z. Because of this, by comparison with central pixel $t_c$, peripheral pixel p provides data from points in space that are more distant from each other. This disparity due to the radial nature of image reconstruction not only impacts the accuracy of reconstruction, but also complicates the task of noise suppression and filtering. Information for noise suppression, for example can be very accurate for voxels that are reconstructed from projection data taken near the center of the subject. But for voxels along the periphery, there is less reliability in obtaining information from corresponding neighboring pixels in adjacent projection images.

In actual practice, the central x-ray may not be incident at $t_c$, but may be offset by some distance for one or more projection images. This capability for offset is used, for example, to enhance the field of view of the 3-D imaging process.

FDK Reconstruction

To more particularly describe aspects of the present invention, it is instructive to review the basic procedure for 3-D image reconstruction that is used in conventional Feldkamp (FDK) reconstruction. Using the conventional circular trajectory of FIGS. 2A-2D, the Feldkamp or FDK reconstruction algorithm has three basic steps:

(1) weighting $P_\beta(u, v,)$;
(2) convolving the weighted projections with a filter kernel h; and
(3) backprojecting the filtered data from every angle β, according to the formula:

$$g(t, s, z) = \frac{1}{2} \int_0^{2\pi} \frac{D_{so}^2}{(D_{so} - s)^2} \int_{-\infty}^{\infty} P_\beta(u, v) * h\left(\frac{D_{so}t}{D_{so} - s} - u\right) * \frac{D_{so}}{\sqrt{D_{so}^2 + v^2 + u^2}} du d\beta, \quad (1)$$

wherein $D_{so}$ is the distance from the source to the origin of the object coordinate system. The (u, v) coordinate system of the detector is given by the following transformations:

$$u = \frac{D_{so}t}{D_{so} - s} \quad (2)$$

$$v = \frac{D_{so}z}{D_{so} - s} \quad (3)$$

In the Cartesian coordinate system (x, y, z), the rotated coordinate system (t, s, z) is expressed by:

$$t = x \cos \beta + y \sin \beta \quad (4)$$

$$s = -x \sin \beta + y \cos \beta \quad (5)$$

This coordinate transform is shown in FIG. 2B.

FDK reconstruction has been shown to be a useful tool for combining the image data from numerous images taken about a circular trajectory of the subject. However, this technique suffers from noise content, a problem that has not been satisfactorily corrected using existing filtering or other noise-compensation techniques. The method of the present invention supports FDK reconstruction by supplying a set of filtered projections with suppressed noise content.

Anisotropic Diffusion

In order to better understand how angular diffusive filtering of the present invention operates, it is instructive to contrast it with other diffusion filtering methods used for image processing. As described in the 2-D noise suppression filtering work of Perona and Malik, cited earlier, anisotropic diffusion is a locally adaptive smoothing process that attempts to minimize blurring near object boundaries. A mathematical formulation in a continuous domain, known to those familiar with Gauss's theorem from vector calculus, expresses the diffusion process on a vector field V at a point c in coordinate-free form by:

$$\frac{\partial f}{\partial t} = div V = \lim_{\Delta t \to 0} \int_s V ds \quad (6)$$

wherein Δt is the volume that is enclosed by the surface s that surrounds a given point c and ds=u ds, where u is a unit vector that is orthogonal and outward-directed with respect to the infinitesimal surface element ds. The intensity flow vector field V controls the diffusion process and is defined as:

$$V = GF \quad (7)$$

where G is the diffusion conductance function, and F is the scene intensity gradient vector field. In a conventional linear isotropic diffusion process, G is a constant. In the Perona and Malik article noted earlier, the authors indicate that such diffusion strategies blur object boundaries and structures. Thus, the noise suppression method proposed by Perona and Malik is an alternative anisotropic diffusion method in which G varies at each location in the scene as a nonlinear function of the magnitude of the scene intensity gradient so that smoothing within a region with low intensity gradients is encouraged, and smoothing across boundaries, wherein the magnitude of the gradients is much higher, is discouraged.

Figure 3:
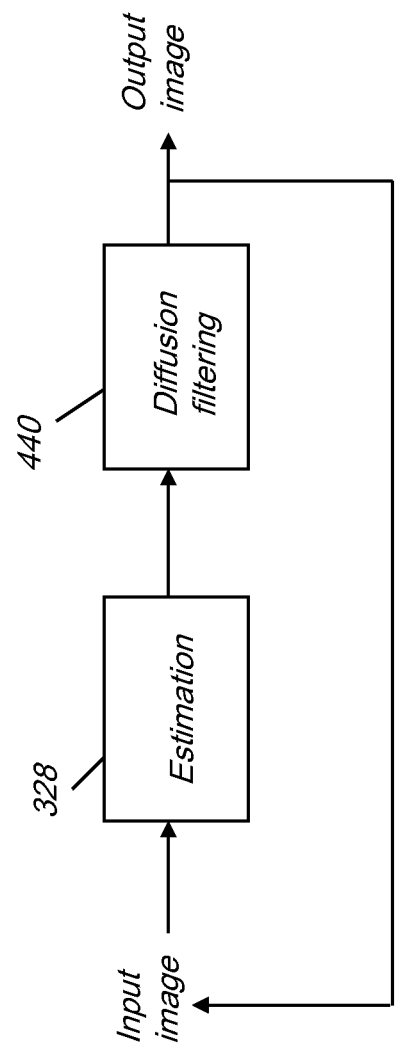
FIG. 3 is a logic flow diagram showing steps for applying diffusion filtering.
Figure 4:
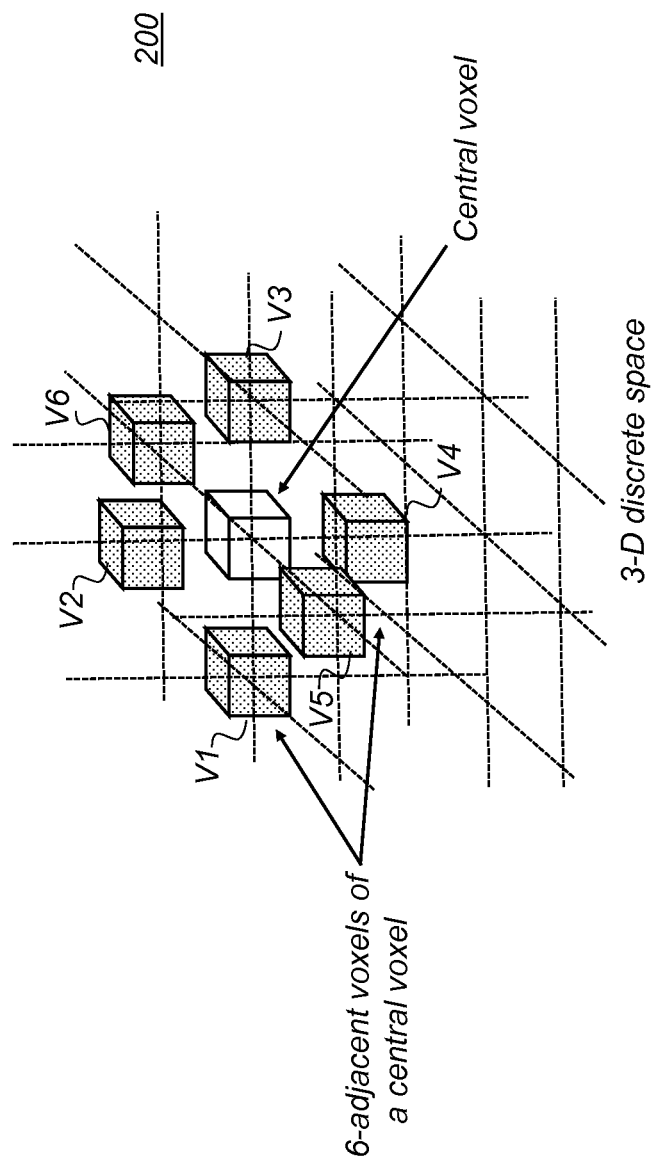
FIG. 4 is a perspective view showing 6-adjacent voxels relative to a central voxel in a 3-D image.

It is instructive to consider how anisotropic diffusive filtering, as suggested for 2-D images by Perona and Malik, can be extended to a 3-D data set for 3-D image reconstruction and to further understand some of the limitations of this approach. The flow diagram of FIG. 3 shows the sequence of processes that are applied for noise suppression when using anisotropic diffusive filtering. In an estimation step 328, appropriate diffusion parameters are computed. Estimation step 328 computes parameters using statistical values that relate to intensity differences in the image data. This includes computing or otherwise obtaining a homogeneity value, a for the 3-D data set for the complete image. A diffusion filtering step 440 then applies the diffusion parameters that have been computed to the 3-D data set. This is an iterative process, repeating one or more times in order to provide improved noise suppression. In subsequent processing, the filtered image from the previous iteration is further filtered. This processing uses the 6-adjacent voxel neighborhood in 3-D discrete space. The 6-adjacent voxels have surface adjacency, as described earlier. FIG. 4 illustrates an exemplary 3-D representation 200 for a 6-adjacent voxel V1-V6 neighborhood for a central voxel.

For comparison of noise reduction methods, FIG. 5(a) shows the results of FDK processing, with the identified area enlarged in 5(d), showing a significant noise pattern. FIG. 5(b) shows the results of applying anisotrophic diffusion to the image. FIG. 5(e) shows an enlarged portion of the image of FIG. 5(b), with a tangential blur that appears from left to right in the image shown.

Tangential blur is an artifact that results due to the circular imaging path that is used for CBCT and due to the corresponding arc length differences for pixels on the detector, as was described earlier with reference to FIG. 2D. Because the radiation is directed as a cone beam through the subject, as was described earlier with respect to FIGS. 2A-2D, the arc length between adjacent out-of-plane pixels (that would be used to form voxels V5 and V6 in FIG. 4) varies depending on their distance from the source. As has been shown, the arc length distance for the out-of-plane adjacent pixels in the 2-D projections, negligible for forming voxels that are very near the center voxel of the subject being imaged, is more and more pronounced as voxels are reconstructed from data taken more distant from the center, most pronounced for voxels that are to be formed from data taken along the perimeter of the subject, furthest from the center.

Angular Diffusion

The method of the present invention provides a novel technique for 3-D weighted angular diffusive filtering that is particularly suitable for CBCT and other types of projection images and reduces or eliminates the visible effects of tangential blur. Unlike conventional 3-D filtering and reconstruction techniques, the method of the present invention takes into account the geometry of image acquisition and applies image diffusion more or less aggressively, depending on the spatial relationships between acquired data. This method accounts for gradient directions and voxel locations relative to the center of rotation (z-axis) as projected onto the detector for each component projection image. Similar to the anisotropic method described above, but unlike earlier noise suppression techniques, the method of the present invention is iterative, with steps that repeat one or more times in order to more effectively apply diffusion processes with each iteration and to yield improved results.

Embodiments of the present invention carry out angular diffusion as an iterative method. For the description of this method that follows, variable k denotes the iteration number. Then $C_{(k)}=(C, f_{(k)})$ denotes the scene resulting from one iteration of diffusion processing, at the kth iteration.

The diffusion flow magnitude function |V| has its maximum value at magnitude gradient $|F|=\sigma_\psi.|V|$. is monotonically increasing for $|F|<\sigma_\psi$ and monotonically decreasing for $|F|>\sigma_\psi$. The diffusion conductance function for the flow from c to d at the tth iteration is given by:

$$G_{(k)}(c, d) = e^{-\frac{|F_{(k)}(c,d)|^2}{2\sigma_\phi^2}} \quad (8)$$

$$F_k(c, d) = \frac{f_k(c) - f_k(d)}{\sqrt{\sum_{i=1}^{3} \frac{v_i^2(d_i - c_i)^2}{\min_j [v_j^2]}}} D(c, d) \quad (9)$$

where, for any 6-adjacent voxels c,d∈C such that c≠d, then D(c,d) is the unit vector along the direction from voxel c toward voxel d. $F_{(k)}(c,d)$ is the component of the intensity gradient vector along D(c,d). Voxel size is taken into account in equation (9) where v=($v_1$, $v_2$, $v_3$). Intensity flow vector $V_{(k)}(c,d)$ from voxel c to voxel d at the kth iteration is defined by:

$$V_{(k)}(c,d)=G_{(k)}(c,d)F_{(k)}(c,d) \quad (10)$$

Iterative processing is then defined as follows:

$$f_{(k)}(c) = \begin{cases} f(c) & \text{for } k = 0 \\ f_{k-1}(c) - k_s \sum_{d \in C} V_{k-1}(c, d) \cdot D(c, d) & \text{for } k > 0 \end{cases} \quad (11)$$

where $k_s$ is a time step constant for the diffusion process. Value $k_s$ is non-negative and has an upper bound limit that depends on adjacency criterion in order to keep the process stable. In one embodiment, the value $k_s=\frac{1}{7}$ is used.

The flow direction between any two voxels c, d∈C is always such that this process tries to reduce the gradient between them. That is: $V_k(c,d) \cdot D(c,d)$ is positive when $f_k(c)>f_k(d)$, and negative otherwise, and zero when c=d. Further, this diffusion process as described with respect to equations (8) through (11) is both nonlinear and anisotropic.

In the angular diffusive-iterative process, v1 and v2 are in-plane resolution defined by the detector's pixel size. v3 is the out-of-plane distance between projection angles β defined as the maximum arc-length. v3 is computed in the image space and measures the maximum arc-length described by the central x-ray after two consecutive projections. This is shown schematically in FIG. 2C.

In order to prevent tangential blur in the reconstructed volume, particularly in very noisy projection data that requires much longer diffusion time (i.e., more iterations), further weighting of v3 is applied. This weighting factor w is a function of t, the longitudinal axis of the projection scene (i.e., detector row), given by:

$$w(t) = \begin{cases} 1 - \sqrt{\sin^2\left(2\arctan\dfrac{t-\Delta}{t_c}\right)}, & 0 \le t \le \Delta + t_c, \text{ if } \Delta < t_c \\ 1 - \sqrt{\sin^2\left(2\arctan\dfrac{\Delta-t}{t_c}\right)}, & \Delta - t_c \le t \le 2t_c, \text{ if } \Delta < t_c \\ 0, & \text{otherwise} \end{cases} \quad (12)$$

wherein $\Delta$ is the displacement from the central x-ray beam to the left-most edge of the detector, which is designated t=0. Value $t_c$ is at the center of the detector. In the simplest or "ideal" case, when the central x-ray beam passes through the center of the detector as described earlier with reference to FIGS. 2A-2D, $t_c = \Delta$.

Figure 6:
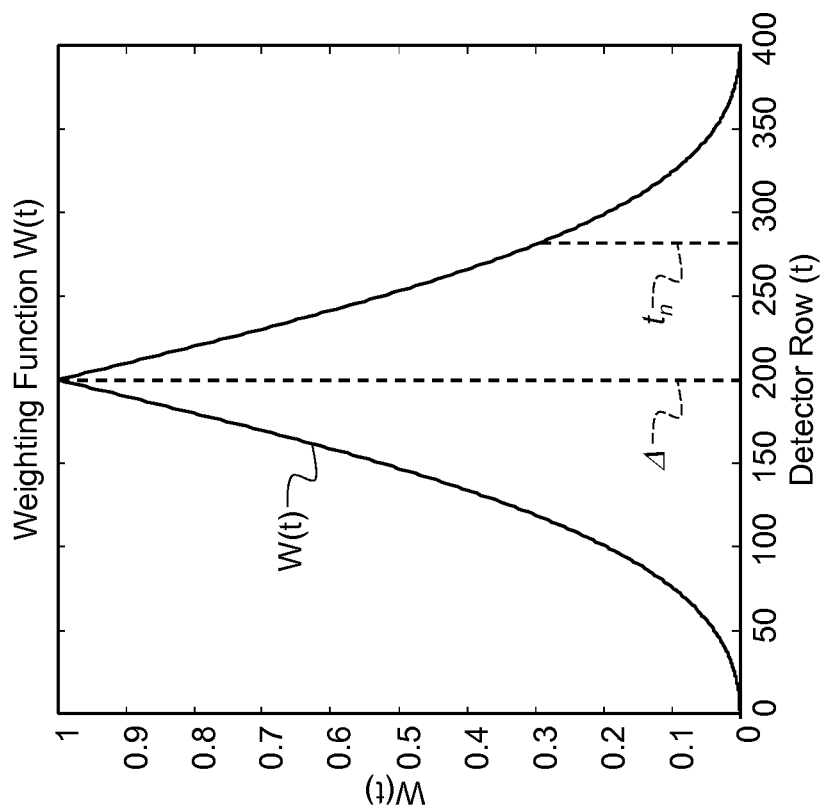
FIG. 6 is a graph showing the weighting function that is applied for out-of-plane pixel data relative to pixel distance from a central pixel for angular diffusive filtering.

The weighting function w(t) is a $\wedge$-shaped (teepee-shaped) function as shown in FIG. 6 with a maximum value of 1.0 at t=$\Delta$. For the simplest case, where $t_c = \Delta$, for a pixel at t lying to the left or right of $t_c$, the value of w(t) varies with the distance from the center $t_c$, with decreased weight assigned as the distance from center increases. For the more general case, such as where the central x-ray does not pass through $t_c$ but is offset from this central pixel position, equation (12) describes how w(t) is computed.

The angular-diffusive iterative process modifies $F_k(c, d)$ in equation (9) as follows:

$$F_k(c,d) = w(t)F_k(c,d) \text{ for } D(c,d) \text{ along the 3rd axis} \quad (13)$$

Figure 7B:
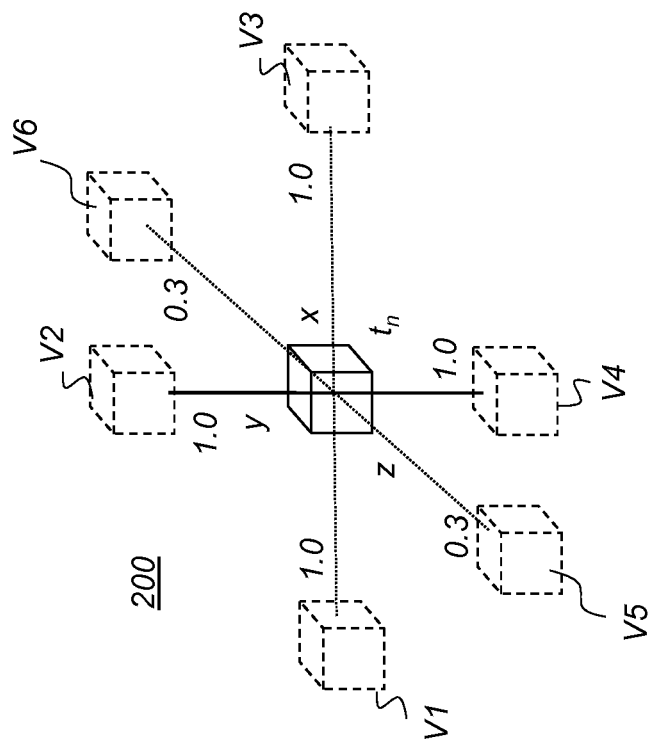
FIGS. 7A and 7B show different weightings applied to data from 6-adjacent voxels in angular diffusive filtering.
Figure 7A:
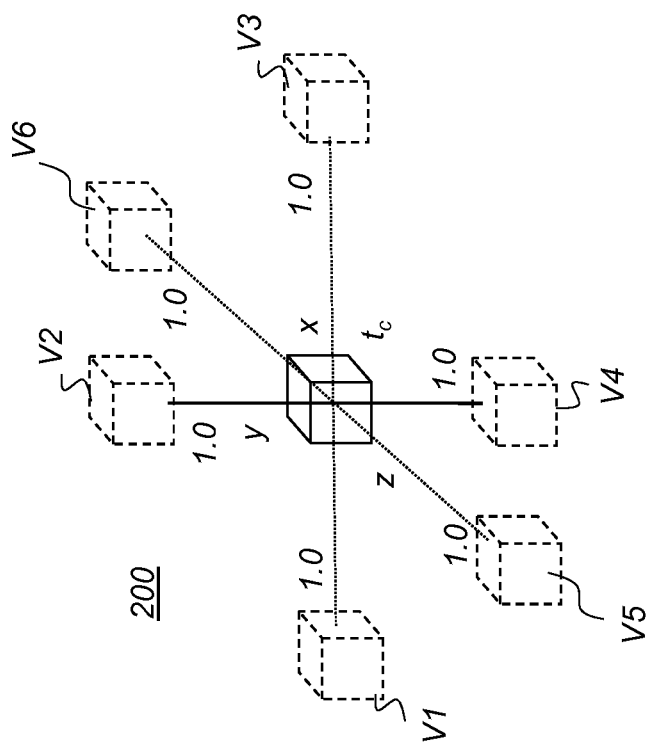

It is noted that the weighting applies for diffusion to voxel locations that are formed from pixel data for pixels out-of-plane relative to the detector at a particular position. Referring to FIG. 7A, weightings for diffusion to the 6-adjacent pupils for a pupil near center $t_c$ are shown. Here, a weighting of 1.0 applies for both in-plane (v1, v2) voxels V1-V4 and out-of-plane (v3) voxels V5 and V6. By contrast, FIG. 7B shows exemplary weightings for diffusion for a pixel $t_n$ further out toward the edge of the detector. Here, a weighting of 0.3 is applied for the diffusion to out-of-plane voxels V5 and V6.

The weighting technique of the present invention causes neighboring in-plane voxels to have more influence on the diffusion algorithm for locations farther from the center of the imaged subject. For voxels closer to the center, voxels from previous and next projections in the series have a greater influence for the diffusion algorithm.

The method of the present invention is advantaged by using built-in knowledge of the geometry of image capture. Unlike other noise compensation algorithms, the relative location of each pixel in a component 2-D projection image influences how diffusion is carried out relative to that pixel location.

Figure 8:
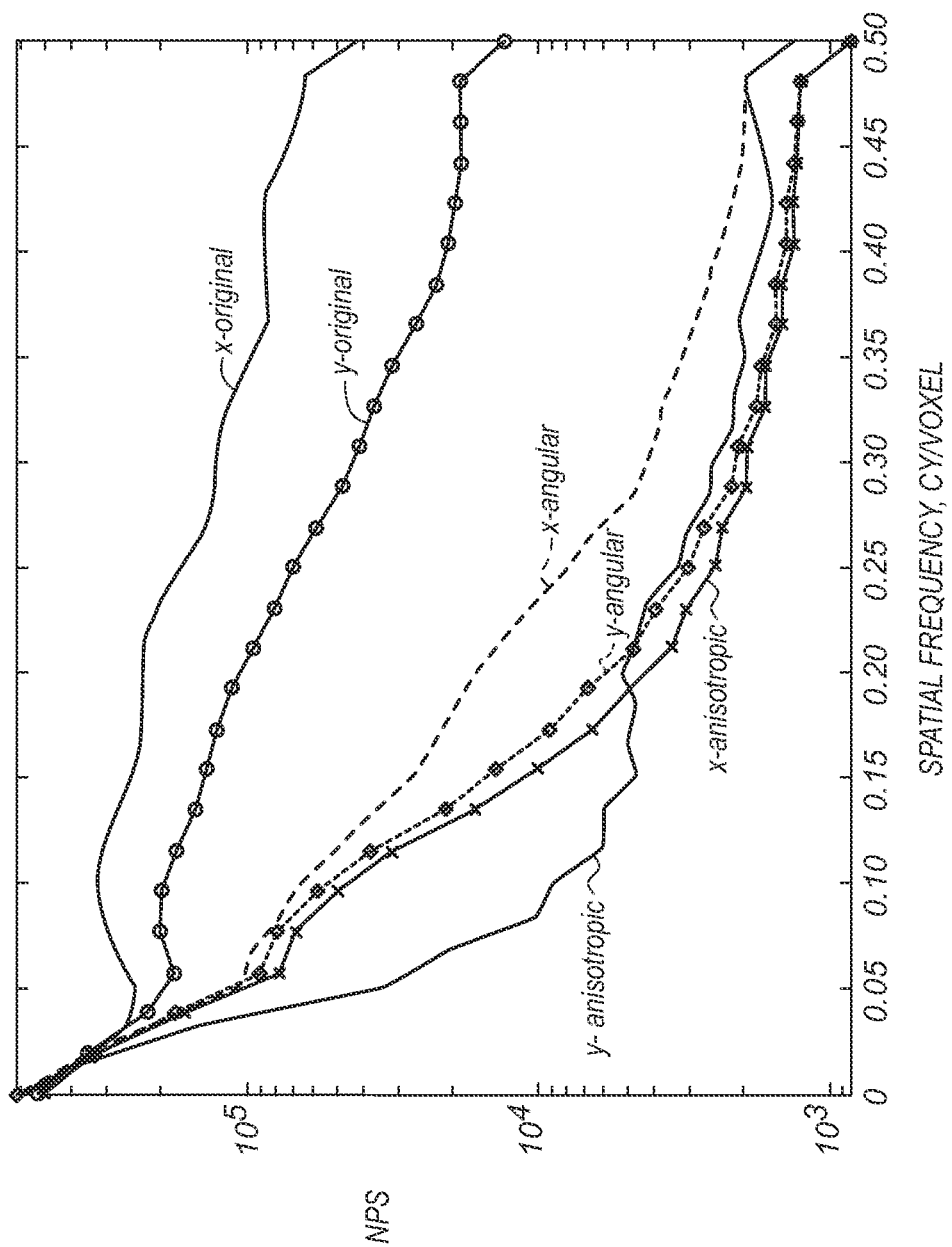
FIG. 8 shows example graphs of noise power spectra and spatial autocorrelation function for conventional and novel approaches to the filtering problem.

The graph of FIG. 8 compares the performance of angular diffusion according to the present invention with anisotropic diffusion methods. At FIG. 8 a noise-power spectrum (NPS) graph shows x-direction and y-direction component noise power spectrum data. The NPS shows image noise, over a nominally uniform area, as a function of spatial frequency. In general, a higher value at high frequencies (approximately 0.25-0.5 cycles/pixel) corresponds to image noise. As is shown, reduction in noise is clearly obtained using either filtering method. FIG. 8 shows that anisotropic diffusion has reduced the noise level, compared to those of the original input (x-orig, y-orig). However, the differences between the x- and y-directions are large at low frequencies, due to tangential blurring. This indicates the presence of a texture that can be seen as one-dimensional smearing, as in the corresponding image of FIG. 5(e). In contrast, the corresponding NPS curves for the angular diffusion of the present invention are closer, that is, are more consistent, particularly at low frequencies. This results in a more uniform appearance that has less one-dimensional texture. This effect is achieved while performing the noise reduction at high frequencies.

Figure 5:
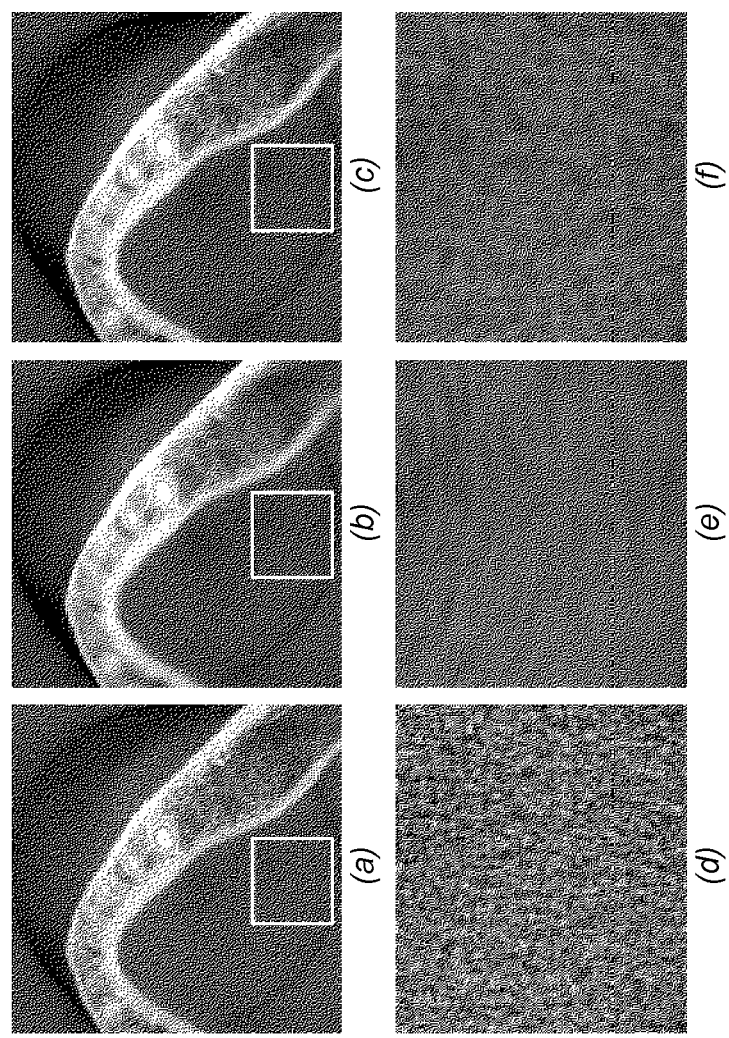
FIG. 5 shows views of conventional reconstruction and filtering techniques compared against the angular diffusive filtering of the present invention.

The grayscale images in FIG. 5 show results from applying the method of the present invention in one embodiment, shown in the right-most column ((c) and (f)) against the original image (left column (a) and (d)) and against results from anisotropic diffusion (middle column (b) and (e)). As this figure sequence shows, tangential blurring is eliminated and noise is reduced using the method of the present invention.

Logic Flow Diagrams

Figure 9:
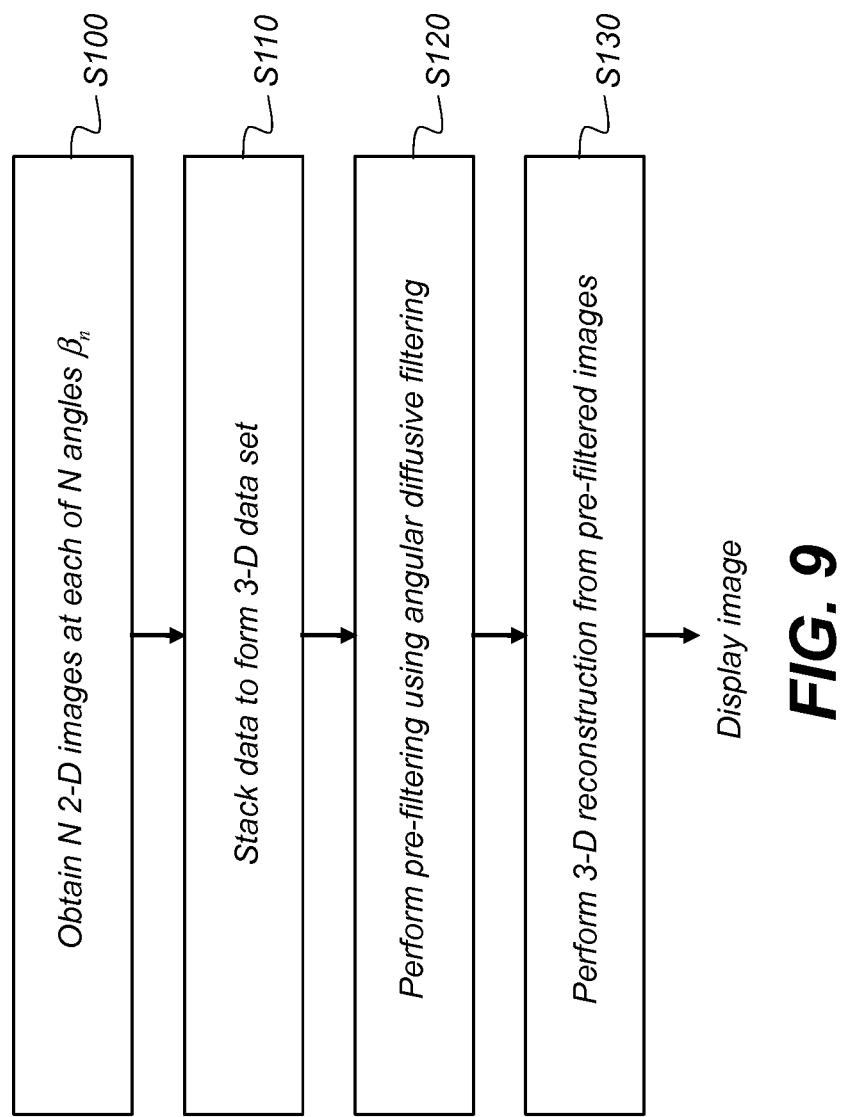
FIG. 9 is a logic flow diagram showing steps for using the angular diffusive filtering of the present invention with 3-D image reconstruction.

FIG. 9 is a logic flow diagram that shows a sequence of image capture and reconstruction that uses the angular diffusion methods of the present invention. A image capture step S100 obtains the data for the set of 2-D projection images, each displaced from its adjacent image by angle β. An image stacking step S110 then arranges the 2-D projection data images in order to form a 3-D data set. Estimation is part of image stacking step S110. A pre-filtering step S120 then applies the angular diffusive filtering described herein in order to suppress noise prior to a reconstruction step S130. Step 120 is iterative, and may execute only once or may repeat one or more times until satisfactory results are achieved. In step S130, the pre-filtered data then goes to the image reconstruction utility for forming the 3-D image, which can then be further processed and displayed.

Figure 10:
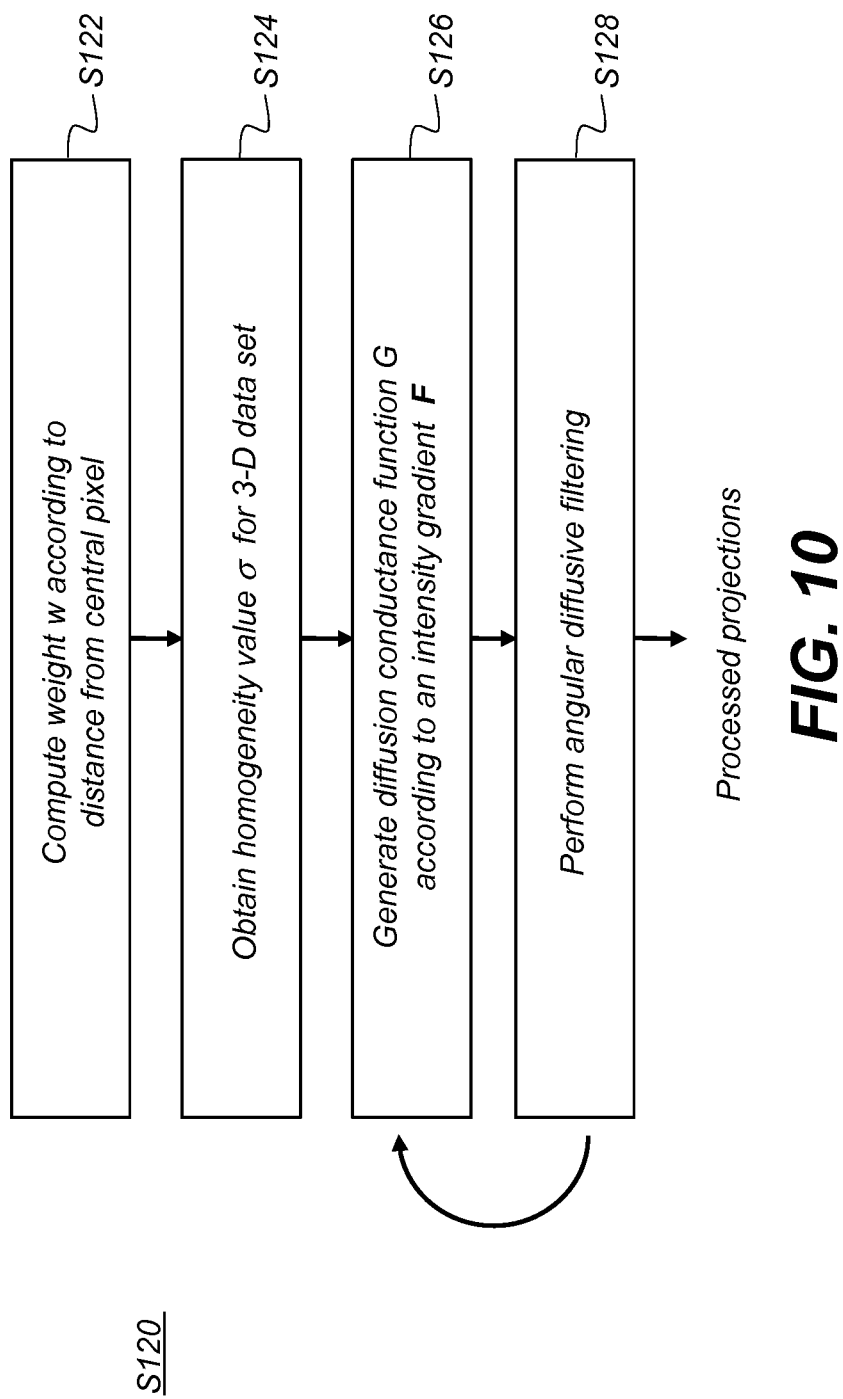
FIG. 10 is a logic flow diagram that shows processes for pre-filtering using angular diffusion.

FIG. 10 is a logic flow diagram that shows, in more detail, the processes for pre-filtering using angular diffusion within step S120 in one embodiment. In a computation step S122, a weighting value is computed that relates to the distance of each pixel in the projection from the central pixel $t_c$. A homogeneity value step S124 computes or otherwise obtains a homogeneity value, typically σ, for the complete 3-D data set. A conductance function step S126 generates a diffusion conductance function according to the intensity gradient between adjacent digital image elements. A filtering step S128 then applies the angular diffusive filtering algorithm to projections in the 3-D data set. Diffusive filtering depends on the obtained homogeneity value, the generated diffusion conductance function, and the computed weighting value. Repeated operation, using the loop represented in FIG. 10, refines and improves the filtering process for providing processed projection data.

Advantageously, the noise suppression method of the present invention does not require more information than does subsequent reconstruction processing. Thus, this processing can be performed in concert with the FDK or other reconstruction algorithms that are used. The method of the present invention has been described primarily as it relates to cone-beam x-ray image processing; however, this method can also be used for other types of imaging where 3-D reconstruction techniques are employed.

The various techniques described herein may be implemented in connection with hardware or software or, where appropriate, with a combination of both. Thus, the methods and apparatus of the invention, or certain aspects or portions thereof, may take the form of program code (i.e., instructions) embodied in tangible media, such as magnetic media, CD-ROMs, hard drives, or any other machine-readable storage medium, wherein, when the program code is loaded into and executed by a logic processor, such as a computer or image processing workstation, the logic processor becomes an apparatus for practicing the invention.

The method of the present invention can be executed automatically and its results stored electronically and displayed on a display terminal without operator intervention. Alternately, the operator can enter information or values that condition the performance of an automated algorithm. For example, the homogeneity value obtained in step 124 (FIG. 10) may alternately be entered or adjusted by an operator in order to affect the performance of diffusive filtering. An optional operator interface, provided in conjunction with a display terminal such as display 120 (FIG. 1), allows the operator to enter an instruction specifying a change to the homogeneity value and to view results computed using a number of different homogeneity values. In one embodiment, the operator interface is a touchscreen with a slider icon for entry of an adjustment instruction from the operator.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

20. Subject
22. Source
24. Detector
100. Image acquisition and processing system
102. Subject
104. CT scanner
106. Computer
110. Data store
118. Selective diffusion computer software
120. Display
200. 3-D representation
328. Estimation step
440. Filtering step
S100. Image capture step
S110. Image stacking step
S120. Pre-filtering step
S122. Computation step
S124. Homogeneity value step
S126. Conductance function step
S128. Filtering step
S130. Reconstruction step
$t_c$. Central pixel
V1-V6. 6-adjacent voxels

What is claimed is:

1. A method for filtering a first 2-D x-ray projection image of a subject for use in a 3-D image reconstruction, comprising:

obtaining the first 2-D projection image data and identifying a central pixel of a detector;
obtaining projection image data for a second 2-D projection image at an offset angle in relation to the first 2-D projection;
arranging the 2-D projection image data for at least the first and second 2-D projection images in an electronic memory to form a 3-D data set;
applying a diffusive filtering process to at least a first pixel of the first 2-D projection image data and weighting the diffusive filtering process for the first pixel, relative to an out-of-plane pixel of the second 2-D projection image, according to the distance between the first pixel and the central pixel;
reconstructing the diagnostic 3-D image using the processed 2-D image projection data; and
transmitting, storing, or displaying the reconstructed diagnostic 3-D image.

2. The method of claim 1 further comprising repeating applying the diffusive filtering process one or more times.

3. The method of claim 1 wherein applying the diffusive filtering process further comprises determining an intensity gradient between adjacent digital image elements.

4. The method of claim 1 wherein applying a diffusive filtering process comprises:
obtaining a homogeneity value for the 3-D data set;
generating a diffusion conductance function according to an intensity gradient between adjacent digital image elements from the projection data; and
applying the diffusion filtering process to a plurality of digital image elements according to the obtained homogeneity value, the generated diffusion conductance function, and a weighting value that relates to the distance of each pixel in the projection from the central pixel.

5. The method of claim 4 wherein the generated diffusion conductance function reduces the magnitude of intensity differences or gradient for one or more pairs of digital image elements.

6. The method of claim 4 wherein obtaining the homogeneity value further comprises receiving an operator entry.

7. The method of claim 4 wherein obtaining a homogeneity value for the 3-D data set comprises computing an average value of magnitude of intensity differences or gradient for two or more digital image elements.

8. The method of claim 7 further comprising computing a standard deviation for the magnitude of intensity differences or gradient for pairs of pixels.

* * * * *

UNITED STATES PATENT AND TRADEMARK OFFICE
CERTIFICATE OF CORRECTION

PATENT NO. : 8,630,473 B2
APPLICATION NO. : 13/693180
DATED : January 14, 2014
INVENTOR(S) : Andre Souza et al.

It is certified that error appears in the above-identified patent and that said Letters Patent is hereby corrected as shown below:

In the Specification

Column 6, Line 48    Please replace the word "(4 s, z)" with the word --(t, s, z)--

Signed and Sealed this
Twenty-seventh Day of May, 2014

Michelle K. Lee
*Deputy Director of the United States Patent and Trademark Office*